(12) United States Patent
Mark

(10) Patent No.: US 7,746,465 B2
(45) Date of Patent: Jun. 29, 2010

(54) SAMPLE HOLDER FOR AN OPTICAL ELEMENT

(75) Inventor: Douglas C. Mark, Tigard, OR (US)

(73) Assignee: Hinds Instruments, Inc., Hillsboro, OR (US)

( * ) Notice: Subject to any disclaimer, the term of this patent is extended or adjusted under 35 U.S.C. 154(b) by 373 days.

(21) Appl. No.: 11/966,557

(22) Filed: Dec. 28, 2007

(65) Prior Publication Data

US 2008/0174773 A1    Jul. 24, 2008

Related U.S. Application Data

(60) Provisional application No. 60/885,591, filed on Jan. 18, 2007.

(51) Int. Cl.
*G01N 21/01* (2006.01)

(52) U.S. Cl. ...................................... 356/244

(58) Field of Classification Search ............ None
See application file for complete search history.

(56) References Cited

U.S. PATENT DOCUMENTS

| | | |
|---|---|---|
| 3,759,620 A | 9/1973 | Cushing |
| 3,925,049 A | 12/1975 | Schwenninger |
| 4,313,679 A | 2/1982 | Wolff |
| 4,692,620 A | 9/1987 | Rosenthal |
| 5,047,652 A | 9/1991 | Lisnyansky |
| 5,201,141 A | 4/1993 | Ahm |
| 5,400,258 A | 3/1995 | He |
| 5,404,581 A | 11/1995 | Nagata |
| 5,470,757 A | 11/1995 | Gagnon |
| 5,519,218 A | 5/1996 | Chang |
| 5,526,119 A | 6/1996 | Blit |
| 5,726,454 A | 3/1998 | Chun |
| 5,805,291 A | 9/1998 | Calvin |
| 5,858,452 A | 1/1999 | Leader |
| 5,898,181 A | 4/1999 | Vurens |
| 5,916,425 A | 6/1999 | Leader |
| 5,956,146 A | 9/1999 | Nakagawa |
| 6,061,131 A | 5/2000 | Igushi |
| 6,111,651 A | 8/2000 | Shakespeare |
| 6,141,867 A | 11/2000 | Fukada |
| 6,317,209 B1 | 11/2001 | Priestly |
| 6,765,734 B1 | 7/2004 | Griffiths |
| 6,992,758 B2 | 1/2006 | Kaplan |

(Continued)

FOREIGN PATENT DOCUMENTS

WO    WO 2004/059266    7/2004

*Primary Examiner*—Gregory J Toatley, Jr.
*Assistant Examiner*—Amanda H Merlino
(74) *Attorney, Agent, or Firm*—Hancock Hughey LLP

(57) ABSTRACT

The sample holder includes support having a thickness and an aperture through the thickness of the support. A tilt mechanism is connected to the support for controlled tilting of the support, and the aperture through the support is configured to have a diameter that increases in a direction through the thickness of the support. This arrangement enables a light beam to pass through the same given area of the sample, irrespective of whether the sample is held perpendicular to the beam or held at a tilted position relative to the beam. In one embodiment, the holder includes an efficient magnetic clamp mechanism for securing the sample to the holder. The holder compactly integrates with tilting mechanisms a sample rotation mechanism.

18 Claims, 3 Drawing Sheets

U.S. PATENT DOCUMENTS

| | | |
|---|---|---|
| 7,016,039 B2 | 3/2006 | Breninger |
| 2001/0007640 A1 | 7/2001 | Edwards |
| 2002/0018192 A1 | 2/2002 | Nishi |
| 2003/0111373 A1 | 6/2003 | Chouinard |
| 2005/0219528 A1 | 10/2005 | Wang |

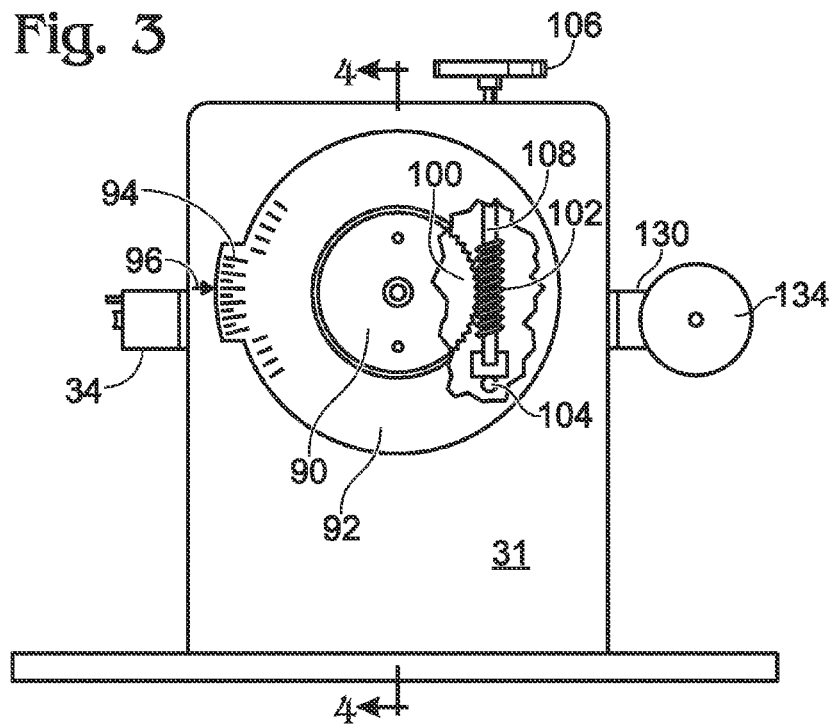
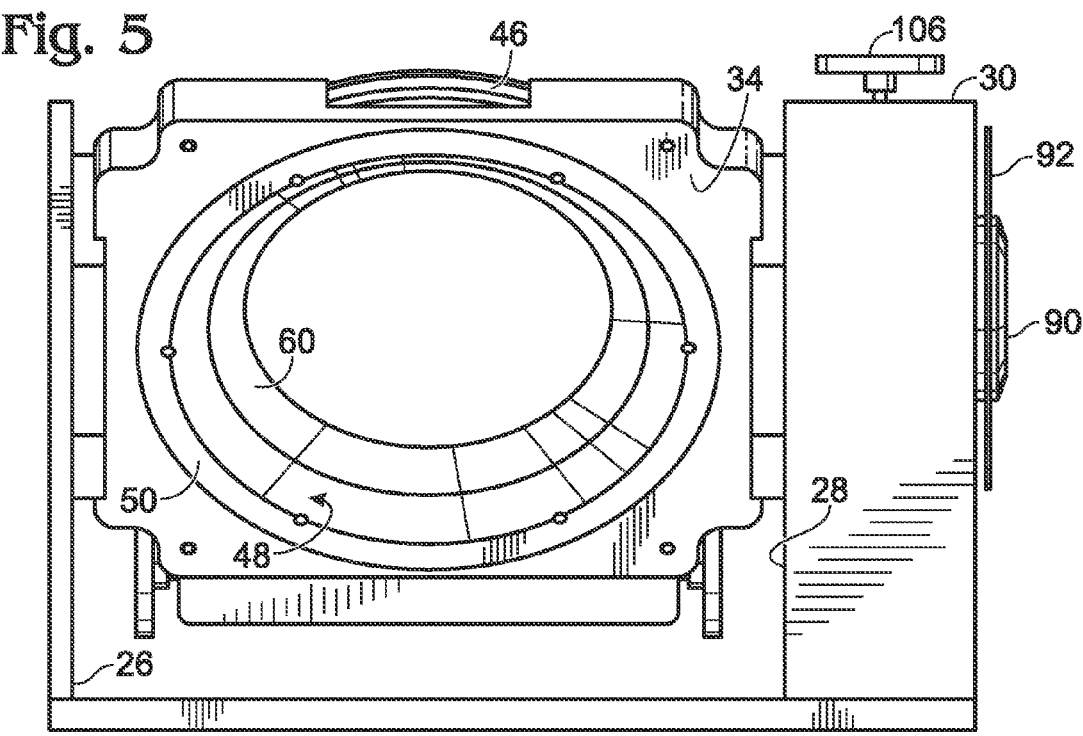

SAMPLE HOLDER FOR AN OPTICAL ELEMENT

TECHNICAL FIELD

This application relates to holding optical material or "samples" in an optical instrument to facilitate the measurement of optical properties of the sample.

BACKGROUND

One important property of optical material is known as birefringence. Birefringence causes different linear polarizations of light to travel at different speeds through the material. These different polarizations are most often considered as two components of the polarized light, one component being orthogonal to the other.

Birefringence is an intrinsic property of many optical materials, and may also be induced by external forces applied to the material. The induced birefringence may be temporary, as when the material is stressed or oscillated, or the birefringence may be residual, as may happen when, for example, the material undergoes thermal stress during production of the material.

Retardation or retardance represents the integrated effect of birefringence acting along the path of a light beam that traverses a sample of the optical material. If the incident light beam is linearly polarized, the two orthogonal components of the polarized light will exit the sample with a phase difference, called the retardance. The fundamental unit of retardance is length, such as nanometers (nm). It is frequently convenient, however, to express retardance in units of phase angle (waves, radians, or degrees), which is proportional to the retardance (nm) divided by the wavelength of the light (nm).

The two orthogonal, polarized beam components mentioned above are parallel to two orthogonal axes associated with the optical material, which axes are referred to as the "fast axis" and the "slow axis." The fast axis is the axis of the material that aligns with the faster moving component of the polarized light through the sample. Therefore, a complete description of the retardance of a sample along a given optical path requires specifying both the magnitude of the retardance and the relative angular orientation of the fast (or slow) axis of the sample.

The need for precise measurement of birefringence properties has become increasingly important in a number of technical applications. For instance, it is important to specify linear birefringence in optical elements that are used in high-precision instruments employed in semiconductor and other industries.

Prior art birefringence measurement systems, including that described in U.S. Pat. No. 6,473,179, disclose methods and apparatus for measuring birefringence of a sample using a light beam that is directed through the sample at a normal (zero-degree) incidence angle relative to the surface of the sample. As a result, the determination of the sample's birefringence is "in-plane," meaning that the determination essentially represents the difference between the indices of refraction of two orthogonal axes in a plane of the sample, that plane being normal to the incident light beam.

The effect of birefringence on displayed visible light (such effects occurring, for example, when the light passes through an optical film or coating) may be to reduce contrast or alter colors. Also, with many materials, such as those used with liquid crystal display (LCD) panels, the extent or magnitude of birefringence is a function of the incident angle of the light under consideration. For example, increasing (from normal) the viewing angle of a LCD panel will increase the birefringence effect on the light emanating from the panel and, without compensation, reduce the perceived quality of the visible light by reducing contrast and/or altering colors.

Transparent polymer films have been developed for use with LCD panels for the purpose of compensating for the just-noted birefringence variations attributable to viewing angle. In short, these films possess birefringence characteristics that compensate for the birefringence of the LCD panel and thus provide a wide viewing angle without significant loss of contrast or color.

It is important to properly characterize the birefringence of such films, and other optical materials, in planes that are parallel to the normal (zero-degree) angle of incidence. This birefringence measure can be referred to as "vertical" or "out-of-plane" birefringence. One can consider the notion of in-plane and out-of-plane birefringence in terms of a Cartesian coordinate system. Accordingly, if the normal-incidence light is considered to travel in a direction parallel to the Z-axis of such a coordinate system, the in-plane birefringence occurs in the XY plane of the sample. Out-of-plane birefringence is in a plane perpendicular to the in-plane birefringence, thus occurring in the XZ or YZ plane.

Other applications (in additional to the birefringence compensation film example just discussed) may call for precise determination of out-of-plane birefringence. For example, certain isotropic crystals, such as calcium fluoride, may exhibit intrinsic birefringence when short-wavelength light (for example, 157 nm) propagates through the crystal. The intrinsic birefringence is greatest in planes that are parallel with the [110] axis of the crystal. Also, such crystals are often produced with an outer surface or "window" for receiving incident light normal to that surface but parallel to the [111] surfaces of the crystal. As a result, the just mentioned intrinsic birefringence present in the [110] axis of the crystal is out-of-plane birefringence relative to the light that is normal to the [110] surface.

One way to accomplish the out-of-plane birefringence measurement is to change the orientation of the light beam (using mirrors or other mechanisms) relative to the stationary sample so that the light beam is directed to be oblique to the sample surface and thus exits the sample with characteristics that provide information relating to the out-of-plane birefringence of the sample. On the other hand, it is also possible to move or tilt the sample relative to the beam, thereby also creating the oblique beam-to-sample-surface relationship.

SUMMARY OF THE INVENTION

The present invention is directed to a sample holder for an optical instrument, and in particular to a sample holder that is useful for holding a sample in a manner that permits precise, controlled tilting of the sample relative to, for example, a light beam that is directed through the sample.

A holder made in accordance with the present invention is configured to enable the light beam to pass through the same given area of the sample, irrespective of whether the sample is held perpendicular to the beam or held at a tilted position relative to the beam.

A holder made in accordance with this invention also includes an efficient magnetic clamp mechanism for securing the sample to the holder.

The holder compactly integrates with tilting mechanisms a sample rotation mechanism. The rotation mechanism rotates the sample about an axis normal to its surface and may be used, for example, to arrange the above-noted fast axis of the sample in a desired location relative to another component in the optical instrument.

Other advantages and features of the present invention will become clear upon study of the following portion of this specification and the drawings.

BRIEF DESCRIPTION OF THE DRAWINGS

FIG. 3 is an elevation view of the front of the sample holder.

FIG. 5 is a side elevation view of the sample holder showing the underside of the sample support when that support is in a tilted orientation.

DETAILED DESCRIPTION

Figure 1:
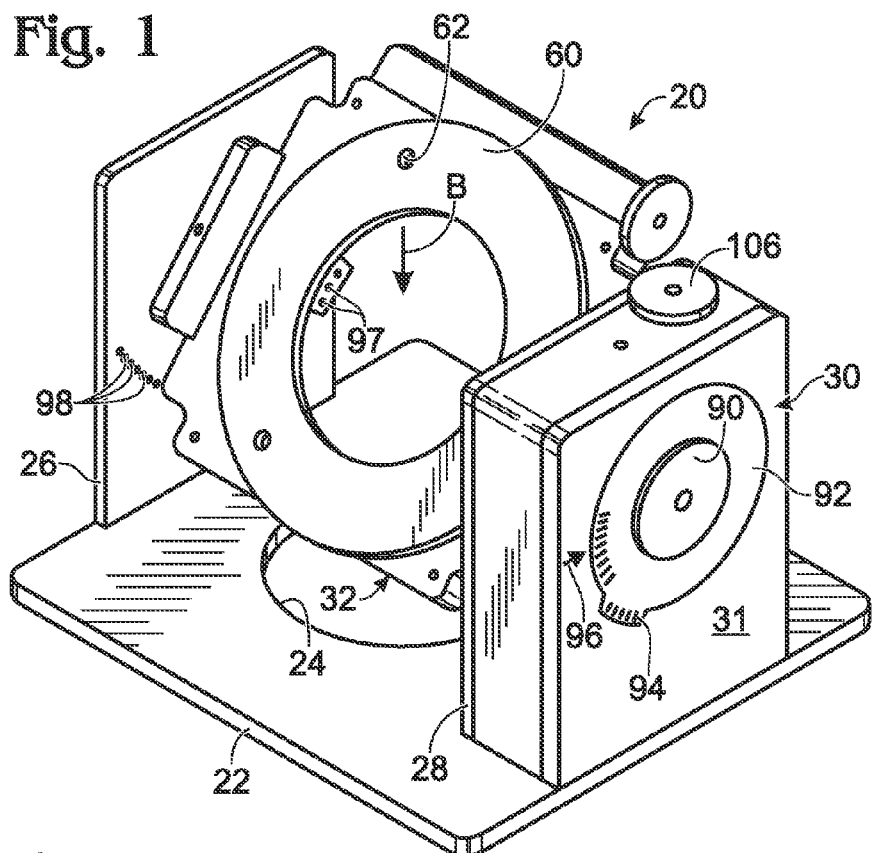
FIG. 1 is a perspective view of one embodiment of a sample holder made in accordance with the present invention, showing the sample support in a tilted orientation.

A sample holder 20 made in accordance with the present invention is shown in FIG. 1 and includes a flat, rigid base 22, that can be mounted in an optical instrument at a location where a beam "B" of light such as laser light may be directed though the holder as well as an opening 24 in the underlying base 22. As noted above, certain aspects of the light beam may be processed before and after passing through optical material or "sample" that is carried on the sample holder 20. Such processing provides information about the birefringence characteristics of the sample.

The present sample holder permits precisely controlled tilting and rotation of the held sample for the analytical purposes mentioned above, including out-of-plane birefringence measurement and fast axis alignment. This description now turns to the particulars of the sample holder, including its sample support, tilting, and rotation mechanisms.

With continued reference to FIG. 1 a flat back wall 26 is mounted to extend upwardly from the base 22 at one edge of the base. Similarly, a flat housing wall 28 extends upwardly from the base 22 near an opposing edge of the base. That housing wall 28 forms part of a cuboidal housing 30 that encloses a tilt mechanism described more fully below.

Figure 4:
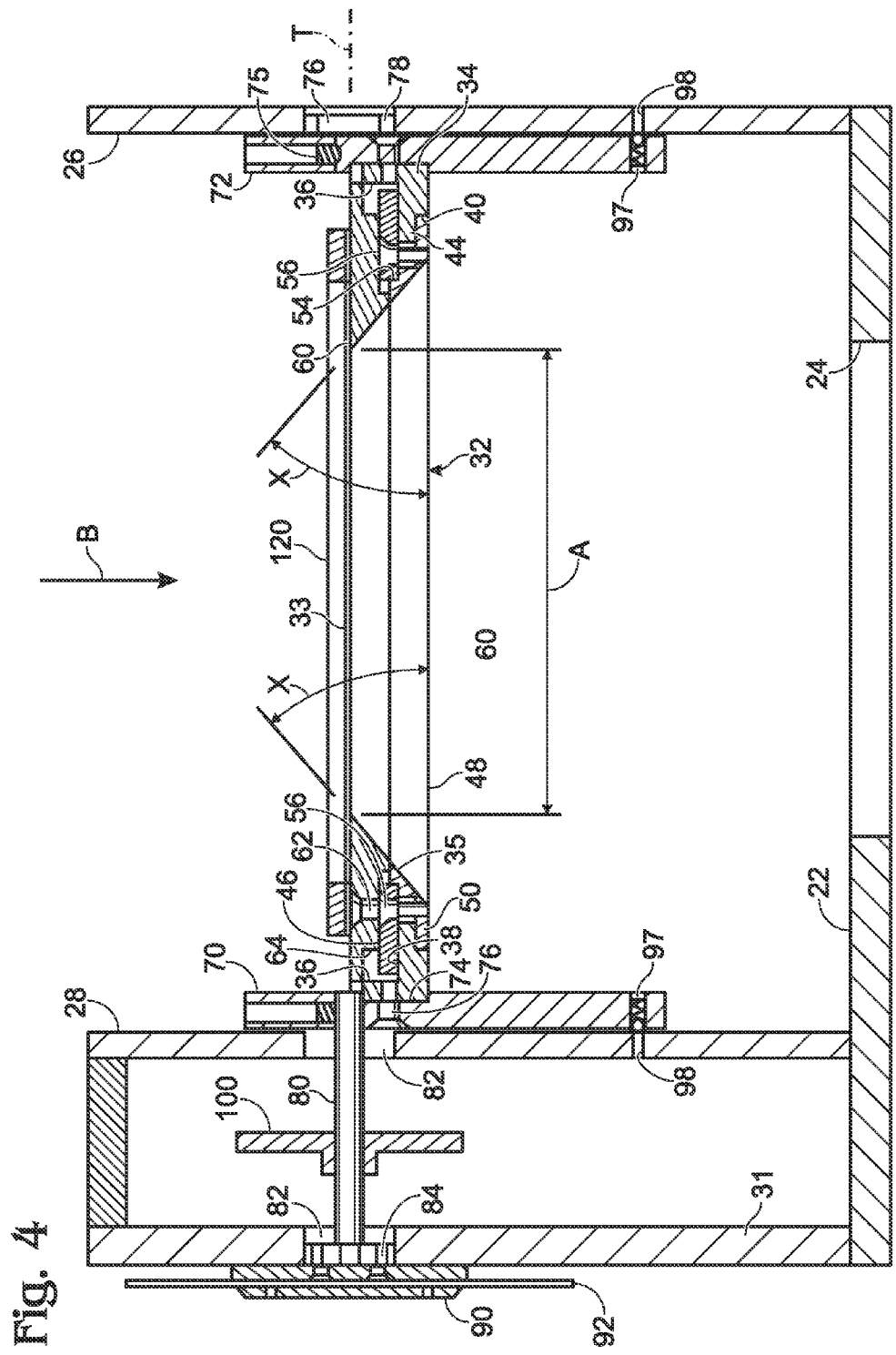
FIG. 4 is cross sectional view of the holder taken along line 4-4 of FIG. 3.

The sample support 32 is an assembly of parts that supports an optical sample. A sample, in the form of a thin transparent film, is illustrated in FIG. 4 (and only in FIG. 4) at reference number 33. The sample support 32 is mounted for both tilting and rotational motion between the back wall 26 and housing wall 28.

Figure 2:
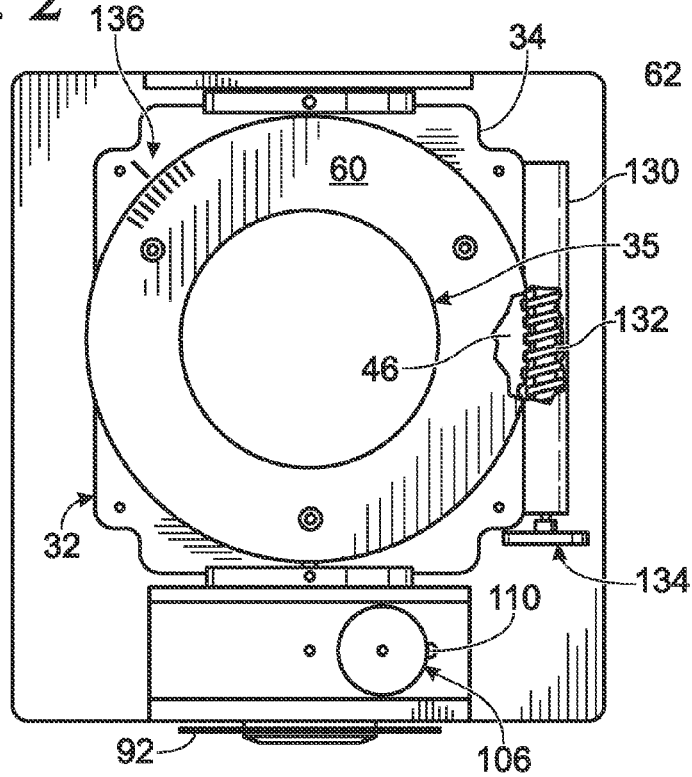
FIG. 2 is a top plan view of a sample holder made in accordance with the present invention, showing the sample support in a horizontal (not tilted) orientation

As best illustrated in FIGS. 2 and 4, the sample support 32 includes a generally rectangular frame 34 that has a central aperture 35 extending completely through it. The frame 34 also includes an annular recess 36 in its upward facing surface. The recess 36 has a larger diameter than that the central aperture 35 and thereby defines an annular shelf 38 protruding inwardly toward the center of the frame.

Another annular recess 40 is formed in the underside of the frame 34. That recess has a diameter that is larger than the diameter of the central aperture 35. Consequently, the recesses 36, 40 define between them in the frame 34 an inwardly protruding annular rib 44.

A flat, annular worm wheel 46 is located on the shelf 38 of the frame rib 44. A generally annular bottom plate 48 having a radially protruding flange 50 abuts the underside of the frame so that the flange 50 fits into the recess 40 in the underside of the frame 34. An annular rabbet 54 is formed at the upper peripheral edge of the bottom plate for receiving the radially inner, lower edge of the worm wheel 46.

Several countersunk fasteners 56 (FIG. 4) extend from the surface of the worm wheel 46, having shafts that pass just inside the frame rib 44 to thread into the flange 50 of the bottom plate 48. As a result, the worm wheel 46 and bottom plate 48 are fastened together in a manner such that the rib 44 is sandwiched between the worm wheel 46 and bottom plate 48. The overall bottom plate dimensions are selected so that when the worm wheel 46 and bottom plate 48 are fastened together with the frame rib 44 therebetween, the worm wheel (which, preferably is formed of brass) and the connected bottom plate will be rotatable within the frame 34 about the central axis of the sample support, subject to the rotation control mechanism discussed below.

A generally annular top plate 60 having a maximum diameter just slightly less that the diameter of the recess 36 in the upper surface of the frame fits into that recess 36 and is attached, by countersunk fasteners 62 to the upward facing surface of the worm wheel 46. Accordingly, the top plate 60 rotates with the worm wheel 46 and bottom plate 48 as a single unit.

A 90-degree groove 64 (FIG. 4) is formed in the top plate 60 at the portion of that plate near the radially outermost edge of the worm wheel 46. This outermost edge defines the teeth of the worm wheel 46 and, therefore, the gap provided by groove 64 serves to expose the teeth of the worm wheel 46 so that the worm wheel may engage an adjustment worm 102 described below.

A hub 70, 72 is mounted to each of the back wall 26 and housing wall 28 between the sample support 32 and the respective wall. Each hub is a generally T-shaped, flat member and has a rectangular notch 74 formed in the inner side of for receiving therein an outer edge of the frame 34. Countersunk fasteners 76 are used to secure the frame edge within the groove, hence securing the entire sample support 32 between the two hubs 70, 72.

The hub 72 that is adjacent to the back wall 26 is attached as by a set screw 75 to one end of a stepped or headed axle member 76 that is mounted to the back wall 26 via a conventional bearing assembly 78. It is contemplated that any of a number of axle and bearing arrangements to attach the axle to the hub 72 may be employed. In any event, the hub 72, hence the fastened support 32, is mounted for rotational movement about the central axis of the axle, which axis being shown as "T" in FIG. 4. For clarity, this motion will be hereafter referred to as "tilting" so as not to be confused with the rotation of the sample support 32 within its frame 34.

The other hub 70 is similarly configured and arranged to mount via an axle 80 and bearing 82 arrangement to the housing wall 28. Thus the support 32 is stably secured between two hubs for tilting motion about axis "T."

The axle 80 for supporting the hub 70 that is mounted to the housing wall 28 includes an extension that passes through the housing so that the head 84 of that axle is journaled in a bearing 82 that is mounted to a front wall 31 of the housing 30. In one preferred embodiment, (FIGS. 1 and 3), the head 84 of the axle has fastened to it a dial 90 and indicator plate 92. The dial 90 permits manual rotation of the axle 80 for tilting the sample support 32 to a desired orientation. The indicator plate 92 includes indicia 94 that when correlated with an index mark 96 on the front wall 31 display the angle at which the sample support is tilted.

A best shown in FIGS. 1 and 4, each hub 70, 72 at its lower end includes a detent mechanism 97 that may be a conventional spring-loaded ball that can be received in any of a series of holes or stops 98 formed in the facing surface of the wall that carries the hub (FIG. 1). In one embodiment the detent mechanism is configured to permit the operator to rotate the dial 90 so that the sample support is secured by the detent mechanism 97 at locations ranging from horizontal to 50 degrees from horizontal, in 5-degree intervals. The dialed tilt adjustment may be considered as a gross tilt angle adjustment.

In a preferred embodiment, the tilt adjustment mechanism just described is supplemented with a finer resolution mechanism comprising a worm wheel 100 (FIGS. 3 and 4) that is mounted to the extension of axle 80 between the housing wall 28 and front wall 31 so that it is contained within the tilt mechanism housing 30. The worm 102 (FIG. 3) is normally engaged with the worm wheel 100. The worm 102 is mounted in the housing 30 with one end pivotally mounted 104 between the housing wall 28 and front wall 31. The other end of the worm carries a knob 106 that is exposed above the housing 30 for rotation by the user. In this regard, the pivotal mount 104 of the worm end is configured to also permit axial rotation of the worm.

As shown in FIG. 3, the worm 102 is normally biased by a spring 108 so that the toothed portion of the worm 102 engages the worm wheel 100 such that rotation of the knob 106 is transmitted to the axle 80 to tilt the sample support 32. This worm gear arrangement permits precise angular adjustment of the tilt position (for example, in one-degree increments) that the user can observe via the juxtaposition of the indicator plate 92 and index mark 96 noted above.

A slot 110 (FIG. 2) is formed in the top of the housing 30 to permit the exposed, knobbed end of the worm to be moved about pivot 104 so that the teeth of the worm 100 disengage the worm wheel 100. This movement reduces resistance to manual rotation of the dial is 90. When the worm is released, the spring 108 urges the worm 102 back into engagement with the worm wheel 100 to enable fine-resolution adjustment if desired.

With reference to FIG. 4, there is shown an annular clamp 120 (only shown in FIG. 4) that rests on the upper surface of the top plate 60 for securing the sample 33 to that plate. The clamp 120 is sized to secure the sample 32 at a distance that is remote from the aperture 35 by an amount sufficient to ensure the clamp does not interfere with the light beam "B" even when the sample support is tilted to a maximum amount.

Preferably, magnetic force is used to secure the clamp 120 and top plate 60 with the edge of the sample 32 therebetween. To this end, the top plate may be constructed of steel, and the clamp ring may comprise, in whole or in part, rare-earth magnetic material.

The sample support 32 is designed to ensure that a given area (such as the area correlating to the diameter "A" in FIG. 4) of the sample 33 will be within a clear, through path of the light beam "B" irrespective of whether the sample is held horizontally (FIG. 4) or tilted by a maximum amount (FIG. 1). In this regard, it is noteworthy that optical instruments of the kind contemplated here include mechanisms for moving the path of the beam across the entire area of the sample so that, for example, birefringence characteristics of the sample may be detected at a large number of locations on the sample. These locations include the edges of the sample (that is, the portion of the sample just inside the aperture 35 defined in the sample holder).

To facilitate the full-area scanning just described above, the aperture 35 through the sample holder 32 is beveled in a manner such that the diameter of that aperture increases through the thickness of the sample holder (that is, the aperture diameter increases in the downward direction in FIG. 4.). Put another way, the aperture 35 in the sample holder 32 defines a frustum shape.

The angle of the aperture bevel (that angle shown as "X" in FIG. 4) is not larger than the complement of the maximum angle that the sample holder may be tilted. In one embodiment, the sample holder may be tilted up to 50 degrees from horizontal. The bevel angle "X" is 40 degrees. The clearance provided by the beveled aperture is available irrespective of whether the sample support is tilted to a maximum position in one direction (clockwise) or another (counterclockwise).

As mentioned above, irrespective of the angle to which the sample support 32 is tilted, the support also permits precise, controlled rotation of the sample 33 within the support and about an axis that is normal to that of the tilting rotation. To this end, a worm gear enclosure 130 is attached to on side of the sample support frame 34 (FIG. 2). That enclosure supports for axial rotation therein an elongate worm 132 in engagement with the teeth of the above described worm wheel 46. A knob 134 protrudes from the enclosure for manual rotation of the worm 132 by an operator, which in turn rotates the sample in the sample support to align, for example, the above mentioned fast axis of the sample with the optical axis of another component of the optical instrument. Human readable indicia 136 on the sample support 32 (FIG. 2) are provided for apprising the operator of the selected rotational position.

While the present invention has been described in terms of preferred embodiments, it will be appreciated by one of ordinary skill in the art that modifications may be made without departing from the teachings and spirit of the foregoing. For example, it is contemplated that the gross and fine tilt adjustment as well as the sample holder rotation mechanisms can be automated with suitable actuators and encoder devices to respectively receive drive signals from and provide position information to an associated controller.

The invention claimed is:

1. A sample holder comprising:
   a support having a thickness and an aperture through the thickness of the support;
   a tilt mechanism connected to the support for controlled tilting of the support; and
   wherein the aperture through the support is configured to have a diameter that increases in a direction through the thickness of the support.

2. The holder of claim 1 wherein the aperture defines a frustum shape in the support.

3. The holder of claim 1 wherein the tilt mechanism is configured to permit tilting of the sample by a maximum amount corresponding to a first angle and;
   wherein the support has a planar surface and the diameter of the aperture defines a sidewall that is inclined relative to that surface by a second angle the second angle being equal to or less than the complement of the first angle.

4. The holder of claim 1 wherein the tilt mechanism provides for rotation of the support about a first axis, the holder including a mechanism for rotating the support about a second axis that is normal to the first axis.

5. The holder of claim 1 wherein the tilt mechanism includes separate gross tilt angle adjustment and fine tilt angle adjustment.

6. The holder of claim 1 including opposing axle members for rotationally mounting the support at opposing edges thereof.

7. The holder of claim 6 including both a gross tilt angle adjustment mechanism and a separate fine tilt angle adjustment mechanism connected to one of the axle members.

8. The holder of claim 5 wherein the fine tilt angle adjustment is selectively disengageable to remove resistance to gross tilt adjustment.

9. The holder of claim 1 including a magnetic clamp for holding a sample to the sample holder.

10. The holder of claim 4 wherein the holder includes a frame that encloses a worm and the support includes a worm wheel mounted thereto to engage the worm, thereby forming a worm gear mechanism for rotating the support about the second axis.

11. The holder of claim 1 further comprising a frame supported by opposing hubs, both hubs comprising detent mechanisms to releasable secure the sample support in a selected tilt position.

12. A method of supporting an optical sample in the path of a light beam so that the sample may be oriented at any selected one of a plurality of orientations relative to the light beam such that the beam path is oblique to the surface of the sample, the method comprising the step of supporting the sample in a holder that has a frustum shaped aperture therethrough and that can be selectively tilted about an axis that is perpendicular to the beam path.

13. The method of claim 12 including the step of magnetically clamping the optical sample to the holder.

14. The method of claim 12 including the step of mounting the sample for rotation within the holder.

15. A sample support comprising:
a holder having a frame and a frustum shaped aperture therethrough;
opposing hub assemblies for supporting the frame about opposing axle members that permit tilting of the holder;
tilting means for enabling precise selection of a tilt position of the frame about a tilt axis; and
detent means for securing the frame in the tilt position.

16. The support of claim 15 wherein the tilting means comprises separate gross and fine adjustment means for respective gross and fine adjustment of the frame into the tilt position.

17. The support of claim 15 including a rotatable member secured to the frame for supporting the optical sample in a manner that permits rotation about an axis that is perpendicular to the tilt axis.

18. The holder of claim 15 including a magnetic clamp for securing a sample to the holder.

* * * * *